(12) United States Patent
Wade

(10) Patent No.: US 12,708,478 B2
(45) Date of Patent: Aug. 18, 2026

(54) SYSTEMS AND METHODS FOR MEDICAL IMAGING

(71) Applicant: Jack Wade, La Jolla, CA (US)

(72) Inventor: Jack Wade, La Jolla, CA (US)

( * ) Notice: Subject to any disclaimer, the term of this patent is extended or adjusted under 35 U.S.C. 154(b) by 0 days.

(21) Appl. No.: 18/382,056

(22) Filed: Oct. 20, 2023

(65) Prior Publication Data

US 2024/0189063 A1 Jun. 13, 2024

Related U.S. Application Data

(63) Continuation of application No. 17/073,199, filed on Oct. 16, 2020, now abandoned, which is a (Continued)

(51) Int. Cl.
*A61B 90/00* (2016.01)
*A61B 1/00* (2006.01)
(Continued)

(52) U.S. Cl.
CPC ...... *A61B 90/361* (2016.02); *A61B 1/000095* (2022.02); *A61B 1/0002* (2013.01); *A61B 1/00042* (2022.02); *A61B 1/0005* (2013.01); *A61B 1/051* (2013.01); *A61B 1/07* (2013.01); *A61B 17/00234* (2013.01); *A61B 2505/05* (2013.01); *A61B 2562/04* (2013.01)

(58) Field of Classification Search
CPC ............ A61B 1/00009; A61B 1/00043; A61B 1/0005; A61B 1/05; A61B 1/051; A61B 1/00181; A61B 1/00174; A61B 1/00045; A61B 1/00097; A61B 1/00096; A61B 1/00048; A61B 17/00234; A61B 2505/05; A61B 2562/04; A61B 1/00193; A61B 1/00194; A61B 1/00052; A61B 1/00011; A61B 1/042; A61B 1/00163
USPC .................................................. 600/103, 109
See application file for complete search history.

(56) References Cited

U.S. PATENT DOCUMENTS 5,547,455 A * 8/1996 McKenna ............ A61B 1/0005 600/113
9,107,578 B2 * 8/2015 Ziberstein .......... A61B 1/00009
(Continued)

*Primary Examiner* — Ryan N Henderson
*Assistant Examiner* — Pamela F Wu
(74) *Attorney, Agent, or Firm* — Olivo IP Law Group, P.C.; John W. Olivo, Jr.

(57) ABSTRACT

The disclosed technology relates to high resolution imagery for a medical environment. Various embodiments provide for a surgical camera, such as an endoscopic camera, comprising an array of image sensors. The array of image sensors may be configured to capture static images or video, may be configured to capture imagery of biological tissue (e.g., surfaces), and may be specifically configured to capture imagery within a surgical environment. For some embodiments, the array of image sensors multiplies the number of available pixels by the number of image sensors, thereby facilitating high resolution image data (e.g., one or more static images or video). The collected image data may be processed at or near real-time to provide very high-quality imagery (e.g., images or video) that can be enhanced or magnified for medical purposes, which can provide a medical care giver (e.g., surgeon) better visibility during medical procedures.

20 Claims, 10 Drawing Sheets

Related U.S. Application Data continuation of application No. 16/149,384, filed on Oct. 2, 2018, now abandoned, which is a continuation of application No. 14/709,241, filed on May 11, 2015, now abandoned.

(60) Provisional application No. 61/991,406, filed on May 9, 2014.

(51) Int. Cl.

| | |
|---|---|
| ***A61B 1/05*** | (2006.01) |
| ***A61B 1/07*** | (2006.01) |
| ***A61B 17/00*** | (2006.01) |

(56) References Cited

U.S. PATENT DOCUMENTS

| | | | | |
|---|---|---|---|---|
| 2005/0225659 | A1* | 10/2005 | Kazami | H04N 5/772<br>348/333.12 |
| 2006/0203087 | A1* | 9/2006 | Kawanishi | A61B 1/0005<br>348/E7.087 |
| 2011/0306832 | A1* | 12/2011 | Bassan | A61B 1/32<br>600/109 |
| 2014/0194896 | A1* | 7/2014 | Frimer | G05B 15/02<br>606/130 |
| 2014/0330078 | A1* | 11/2014 | Hwang | A61B 1/00194<br>600/109 |

* cited by examiner

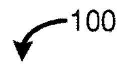
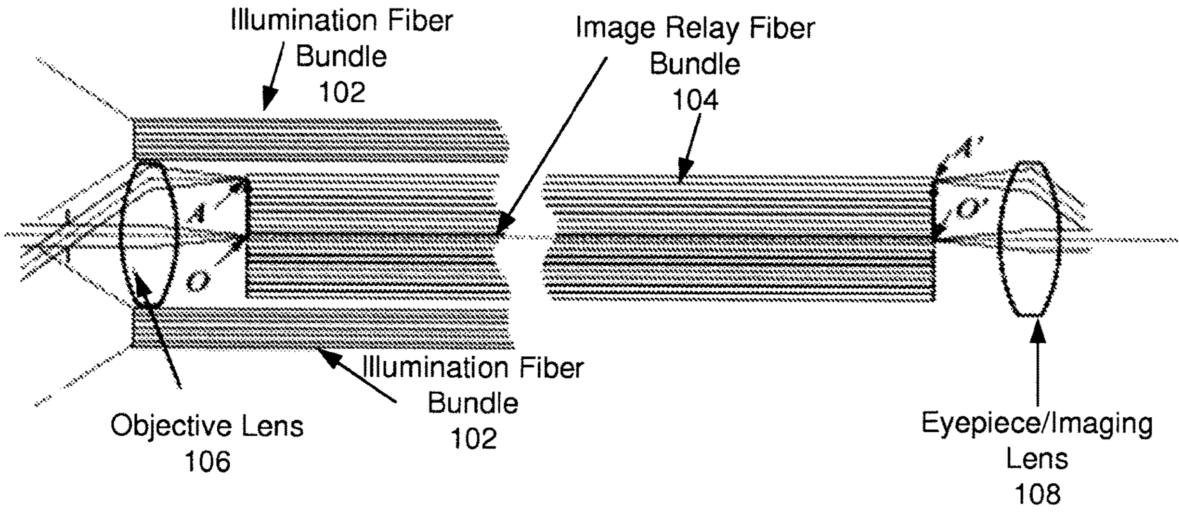
CONVENTIONAL
FIGURE 1

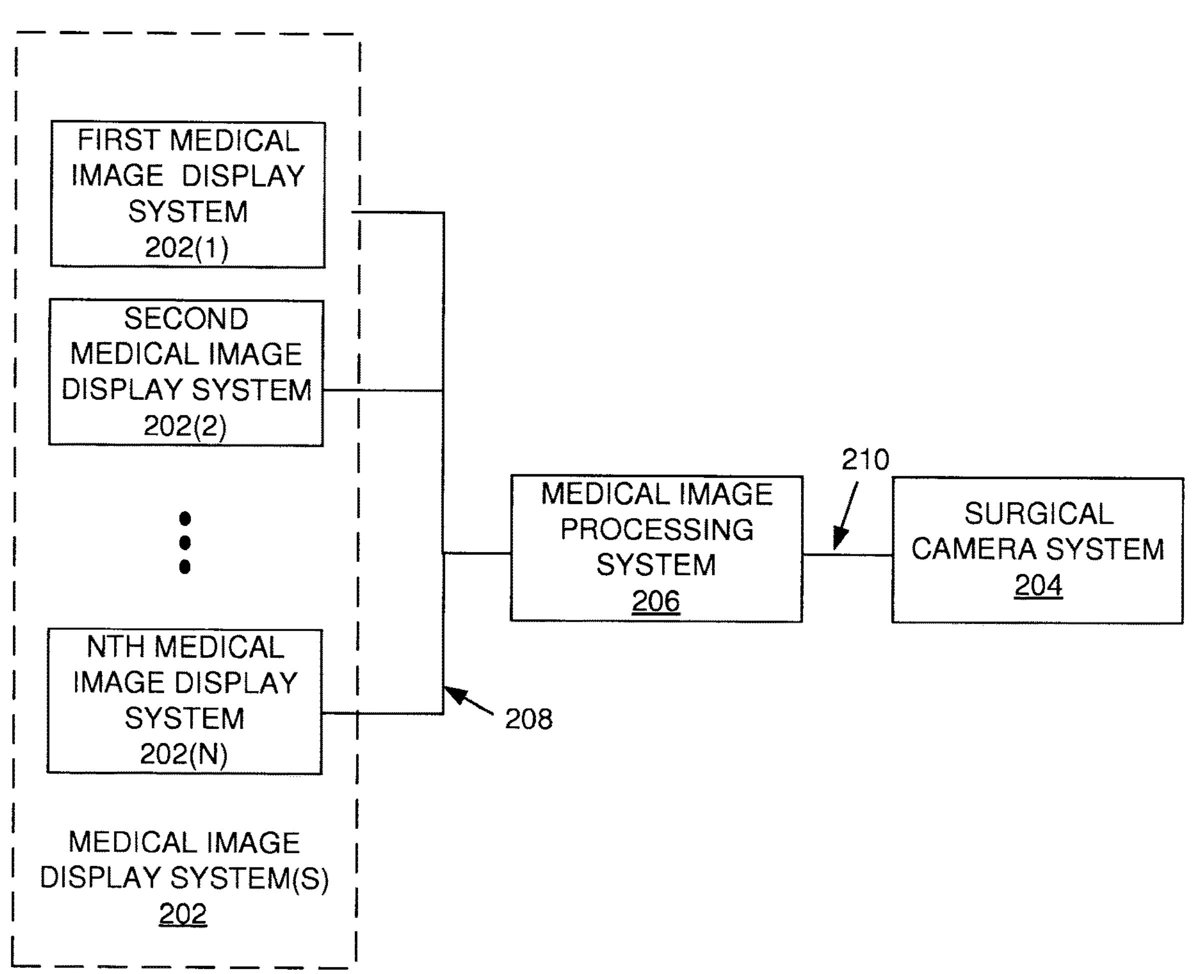
FIGURE 2

START

PROVIDE INSTRUCTIONS FOR A SURGICAL CAMERA SYSTEM TO ACCESS A SELECTED SAMPLE
502

THE IMAGE SENSOR CAPTURES LIGHT FROM THE SELECTED SAMPLE AND GENERATES AN ELECTRICAL SIGNAL REPRESENTATION OF THE IMAGE
504

CAPTURED IMAGE DATA IS PROVIDED TO MEDICAL IMAGE PROCESSING SYSTEM 206 FOR IMAGE PROCESSING
506

COMPRESS THE PROCESSED IMAGE FROM A FIRST PIXEL RESOLUTION TO A SECOND PIXEL RESOLUTION
508

PROVIDE THE PROCESSED, COMPRESSED IMAGE TO THE MEDICAL IMAGE DISPLAY SYSTEM(S) FOR DISPLAY AT THE SECOND PIXEL RESOLUTION
510

END

FIGURE 5

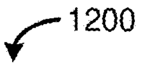
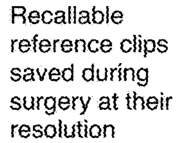
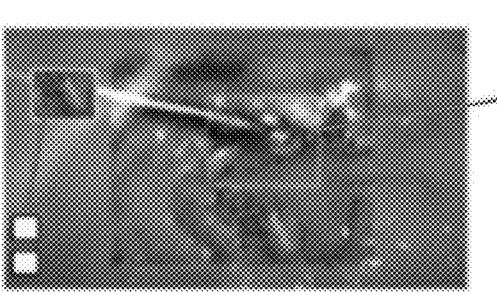
Operating
surgeon
controls this
window
At other locations sharing network access
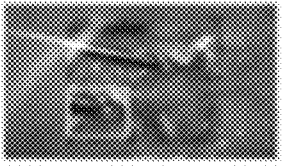
FIGURE 7

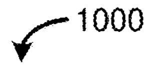
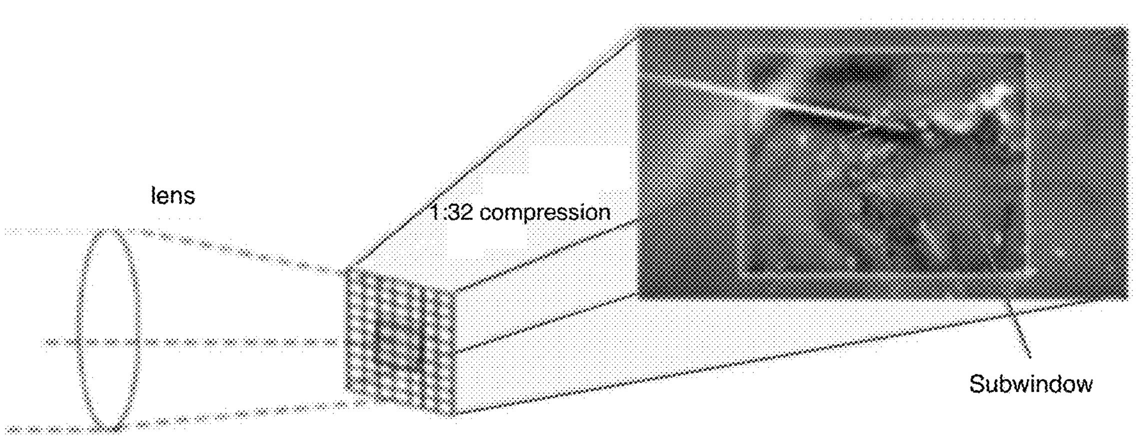
FIGURE 8

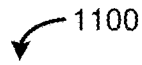
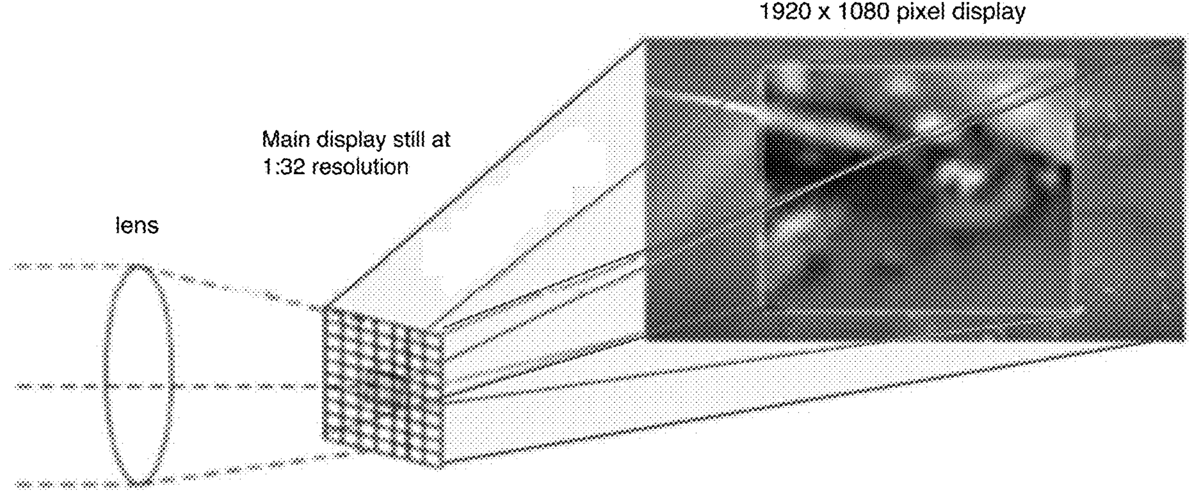
FIGURE 9

SYSTEMS AND METHODS FOR MEDICAL IMAGING

CROSS REFERENCE TO RELATED APPLICATIONS

The preset application is a continuation of U.S. patent application Ser. No. 17/073,199, filed Oct. 16, 2020, which is a continuation of U.S. patent application Ser. No. 16/149,384, filed Oct. 2, 2018, which is a continuation of U.S. patent application Ser. No. 14/709,241, filed May 11, 2015, which claims the benefit of claims the benefit of U.S. Provisional Patent Application Ser. No. 61/991,406, filed May 9, 2014, the contents of which is hereby incorporated by reference herein in its entirety.

TECHNICAL FIELD

The technology disclosed herein relates to imaging tools and, in particular, some embodiments relate to systems and methods for imaging a selected subject matter (e.g., tissue, organs or a body cavity) in a medical environment, such as a surgical environment.

DESCRIPTION OF RELATED ART

Minimally invasive medical procedures have been increasing in popularity and have become commonplace inpatient care. For instance, endoscopes and other types of medical imaging devices are indispensable tools in patient care, especially in in-patient and out-patient surgical environments. Advantages of using endoscopes include the ability to avoid large incisions and the ability to image a tissue such as, for example, biological tissue within a body cavity and biological tissue that is accessed through a small incision formed by a minimally 25 invasive surgical device.

Endoscopes are traditionally long, thin optical instruments that can be introduced into a subject's body to illuminate and image body cavities, organs or other tissue. Endoscopes traditionally include a long, thin set of tubes that illuminate the subject tissue or cavity using illumination fibers. Many endoscopes also include one or more lenses that focus images of the illuminated body cavity onto an eyepiece and/or imaging lens. Still or video cameras can be used to capture the images returned by the endoscope.

Due to their small size (e.g., they can be as small as a few millimeters in diameter), endoscopes enable surgeries to be performed in a manner that is less intrusive and often safer for patients. For, example endoscopes can be introduced through small incisions as well as through body cavities such as, for example, the nose and throat. While this brings many benefits to patients, it presents a number of challenges for the surgeon who must work within a very confined surgical compartment. In particular, surgeons must deal with poor visibility, limited lighting and a narrow viewing angle. Because of their size, conventional endoscopes (and the like) tend to have limited imaging resolution and often fail to provide more than one perspective of biological tissue.

FIG. 1 is a diagram illustrating one example of a portion of a conventional endoscope 100. The conventional endoscope 100 includes illumination fiber bundles 102, image relay fiber bundles 104, an objective lens 106, and an eyepiece/imaging lens 108.

The illumination fiber bundles 102 may include one or more optical cables or fibers configured to transport light from a light source (not shown) at the proximal end to illuminate biological tissue. The illumination fiber bundles 102 may each include, for instance, up to 50,000 separate optical fibers, each configured to provide light to the biological tissue. The objective lens 106 may receive images as reflections of light from the biological tissue that has been illuminated by the illumination fiber bundles 102. Objective lens 106 focuses the image onto the distal end of the fibers of image relay fiber bundle 104 and the focused image is coupled into the fibers of the image relay fiber bundle 104.

The image relay fiber bundles 104 may include one or more optical cables or fibers that transmit images of the biological tissue to the eyepiece/imaging lens 108. The image relay fiber bundles 104 may each include, for example, up to 50,000 separate optical fibers, each configured to relay imagery of biological tissue from the objective lens 106 to the eyepiece/imaging lens 108. The eyepiece/imaging lens 108 may display the imagery of the biological tissue to a camera which can display it on a surgical monitor (not shown in FIG. 1). The eyepiece/imaging lens 108 may focus the reflections so that a user can view the reflections. In alternative conventional endoscopes, a camera or image sensor (not shown) may either be coupled to or take the place of the eyepiece/imaging lens 108. The camera may capture medical images (still medical images and/or medical video) of the reflections on a medical image display system (not shown) that records the images.

Increasingly, conventional endoscopes, such as the conventional endoscope 100 are being replaced by video endoscopes that transmit surgical imagery to a display monitor for easier viewing by the surgeon and other members of the medical team. Video endoscopes are similar to traditional endoscopes, except that they rely on a sensor, such as a Charge Coupled Device (CCD) that is mounted toward the distal end of the endoscope. Video endoscopes may also include supporting electronics and/or a camera head that allow the surgeon to control the view. Video endoscopes offer many advantages over traditional endoscopes, including a larger view, image enhancement for improved clarity, and video recording capability. However, image resolution of the CCD remains as a limiting factor in terms of image magnification and precludes the ability to zoom in to see very fine detail, or at a cellular level.

SUMMARY

Various embodiments of the systems and methods described herein may relate to high resolution imaging in a medical environment. Particularly, various embodiments may include a surgical camera, such as an endoscopic camera, that includes an array of image sensors. The array of image sensors may be configured to capture static images or video, may be configured to capture imagery of organs, body cavities or other biological tissue (i.e., a selected subject), and may be specifically configured to capture images of the selected subject within a surgical environment.

The array of image sensors may be disposed at or near the head of the surgical camera. The array of image sensors may utilize a plurality of image sensors, such as charge-coupled devices (CCDs). With use of the image sensors, embodiments can be configured to obviate the need to relay an image from an objective lens. This can be accomplished, for example, by configuring an objective lens to transmit an image (of the biological tissue) directly to sensing elements in the array of image sensors. For some embodiments, the surgical camera includes an imaging sensor, an objective lens, and illumination optics. The array of image sensors can be configured in some embodiments to provide a greater resolution than is otherwise provided through use of fiber optic bundles used in traditional endoscopes. It will be appreciated that the array of image sensors may comprise, for example, CCDs, non-CCD image sensors such as Complementary Metal-Oxide-Semiconductor (CMOS) sensors, electron multiplication CCD or EMCCD image sensors, or some combination of sensor types. The arrangement of image sensors in the array may vary between embodiments. The image sensors may be arranged, for example, as a plane, as a sphere, as a square, as a rectangle, as a circle, or as a triangle.

In some embodiments, the array of image sensors can be configured to multiply the number of available pixels by the number of image sensors, thereby facilitating high resolution image data (e.g., one or more static images or video). The collected image data may be processed in real-time (i.e., as the images are captured) to provide very high quality imagery (e.g., images or video) that can be enhanced or magnified for medical purposes, which can provide a medical practitioner (e.g., a physician, surgeon, or clinician) better visibility during medical procedures. For example, a user may select a portion of the image contained in the collected image data such as an area of interest (AOI), and may zoom into the selected portion, possibly to a microscopic level. Some embodiments may be configured to enable a medical practitioner to noninvasively identify whether biological tissue is healthy or diseased, and do so without the need to cut or remove a tissue specimen from the body. In this way, some such embodiments may function as an optical biopsy tool.

Various embodiments include an image processing system configured to process and enhance the imagery (e.g., video imagery) in real-time (i.e., as the image data is received, but with buffering as may be necessary or other nominal system latencies) using specific image processing algorithms. The image processing system can include, for example, logic for stitching the various image data from the individual sensors in the array into a single, high resolution, seamless picture. Depending on the embodiment, the image data from less than all the image sensors in the array may be stitched together for viewing or storage, or both. This may occur, for example, when a user wishes to focus on an area of interest (AOI) in the area under observation by the array of image sensors. In some embodiments, to accomplish this, image sensors of the array that correspond to the AOI can be identified and the images from these identified sensors may be stitched together. These identified sensors can be selected and the image data from the other image sensors (i.e., the nonselective image sensors) in the array can be disregarded or stored and saved for later.

The image processing system can include logic for compressing high resolution images to a format suitable for display on display devices that have lower resolutions. The image processing system can further include logic for different types of image enhancement to improve image quality or visibility of important details (e.g., reducing blurriness or smoke). These and other image processing techniques can be used, such as those described in U.S. Pat. Nos. 7,092,582; and 8,107,760, each of which are incorporated herein by reference in their entirety.

Some embodiments enable capture of high resolution imagery that can be magnified to reveal increasing detail. For some embodiments, magnification is facilitated without the need for digital zoom, which uses the same number of pixels in the portion of the image being magnified as there are in that same portion in the unmagnified image and thus results in a loss of clarity in the enlarged image. The magnification in embodiments of the technology disclosed herein may be achieved, for example, by retrieving raw image data (e.g., video or static images) from only those image sensors in the array that correspond to the area selected for magnification. This process may be further facilitated by adjusting a compression utilized to show the raw image data on a display. For example, assume an array of 10 image sensors at 20 megapixels each.

Capturing and transferring images from all of the sensors in the array would require a bandwidth of at least 200 megapixels. This could require compression to enable real-time handling of this amount of data. Whereas if a proper subset of the image sensors is selected to target the AOI and less data needs to be transferred then the transfer may occur without compression or with less severe compression. Assume for example the same 10 image sensors at megapixels each. Further assume that 3 of the sensors are selected to target an AOI. This results in a 60 megapixel image (setting aside overhead) which requires less compression in a bandwidth limited channel than would a 200 megapixel image. Accordingly, in some embodiments, depending on the number of image sensors selected and the bandwidth of the channel, raw images, or images with little or no compression can be provided thereby improving their resolution for the area of interest. The raw image data can contain a large number of pixels that show increased details in the biological tissue being observed. The raw image data can be outputted to a display capable of showing images at the highest resolutions.

In various embodiments, the system may be configured such that each image sensor in the array is focused on a different area of interest (AOI) (e.g., different portion of biological tissue). The areas of interests covered by the array of image sensors may depend on the arrangement (e.g., orientation, location, etc.) of the image sensors within the array. Depending on the embodiment, the arrangement of the image sensors may be operator-adjustable, possibly by manual or mechanized (e.g., motorized) means. In other embodiments, the arrangement of the image sensors may be preset to predetermined orientations. The image data provided by each image sensor may be separately processed and enhanced. Embodiments may further be implemented in which two or more viewers can simultaneously view, process, and enhance different portions of the image data provided by different sets of image sensors in the array. Additionally, various embodiments may be configured to permit two or more viewers using one or more displays to open multiple views to different portions of the image data provided by the array image sensors.

Other features and aspects of the disclosed technology will become apparent from the following detailed description, taken in conjunction with the accompanying drawings, which illustrate, by way of example, the features in accordance with embodiments of the disclosed technology. The summary is not intended to limit the scope of any inventions described herein, which are defined solely by the claims attached hereto.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

Some of the figures included herein illustrate various embodiments of the disclosed technology from different viewing angles. Although the accompanying descriptive text may refer to such views as "top," "bottom" or "side" views, such references are merely descriptive and do not imply or require that the disclosed technology be implemented or used in a particular spatial orientation unless explicitly stated otherwise.

FIG. 1 is a diagram illustrating a portion of a conventional endoscope.

FIG. 2 is a diagram illustrating an example system-level implementation of the various embodiments of the technology disclosed herein.

FIG. 5 is a flowchart illustrating a method for imaging biological tissue in accordance with one embodiment of the technology described herein.

FIG. 7 is a diagram illustrating an example use of one or more example image processing algorithms such as those described above with respect to FIGS. 5 and 6.

FIG. 8 is a diagram illustrating an example array of image sensors observing biological tissue in accordance with one embodiment of the technology described herein.

FIG. 9 is a diagram illustrating an example array of image sensors observing biological tissue in accordance with one embodiment of the technology described herein.

Figure 3:
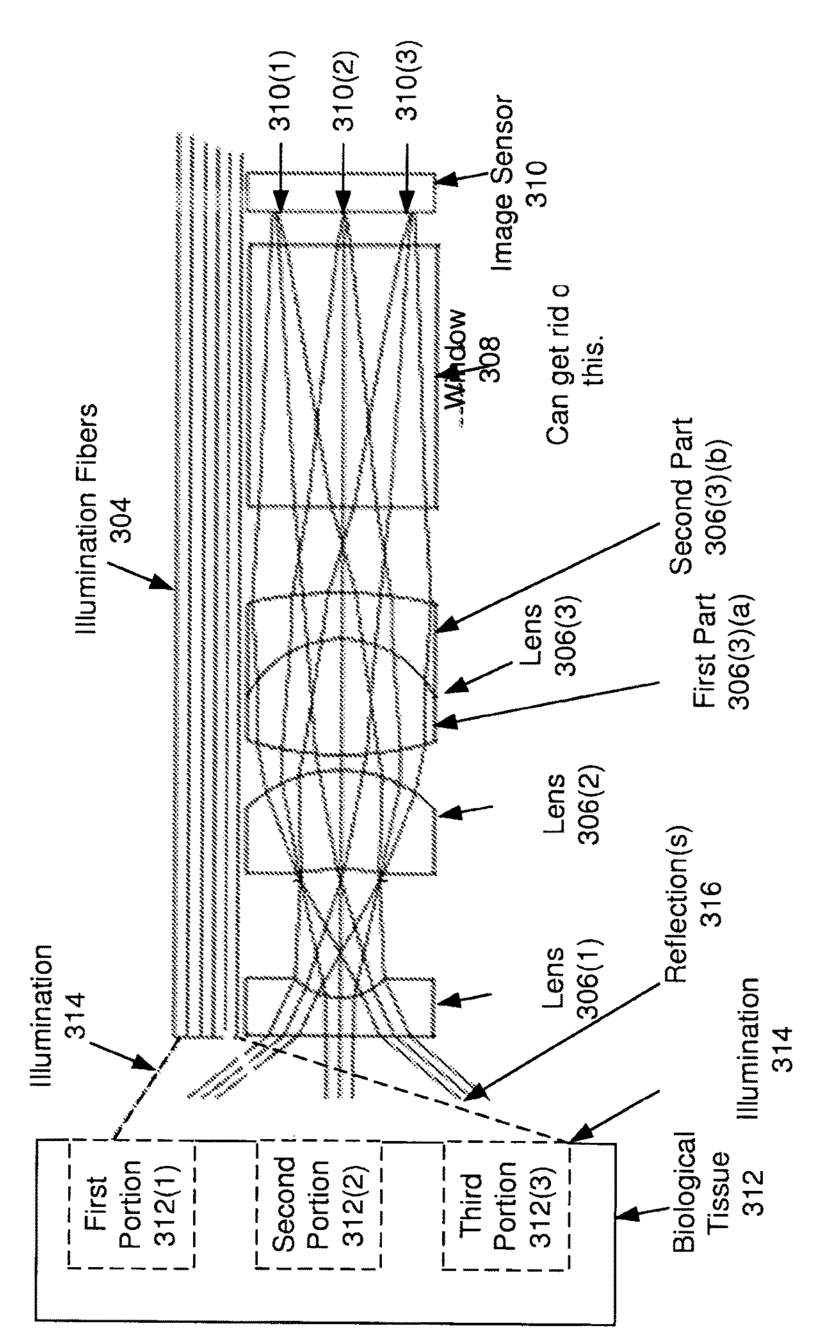
FIG. 3 is a diagram illustrating a surgical camera having image sensors installed thereon in accordance with one embodiment of the technology described herein.

The figures are not intended to be exhaustive or to limit embodiments described herein to the precise form disclosed. It should be understood that any embodiments described herein can be practiced with modification and alteration, and that the disclosed technology be limited only by the claims and the equivalents thereof.

DETAILED DESCRIPTION OF THE PREFERRED EMBODIMENT

Systems and methods disclosed herein provide an imaging system such as an endoscopic imaging system for a variety of applications. Embodiments of the systems and methods disclosed herein can be configured to utilize a plurality of image sensors as an array of image sensors to capture images for display or recording. In various embodiments, algorithms or other processing techniques can be used to provide high resolution imaging and to provide real-time image magnification without the loss of resolution, or without the same amount of loss of resolution as would be experienced by typical conventional "digital zoom" techniques.

Particularly, in various embodiments, an array of image sensors is used to capture images from the endoscope. The optical fiber or lens system used to transmit the images from the objective lens to the image sensor is configured to allow sections or portions of the tissue, organ, cavity, or other sample being imaged to be mapped to corresponding image sensors in the sensor array. Because of this mapping, individual image sensors or groups of image sensors in the sensor array capture images for identified or determined portions of the sample. Embodiments can take advantage of this mapping to provide enlargement of an area of interest (AOI) for viewing. This can be done in real-time, or can be done after the fact with stored image data.

In some embodiments, a health care practitioner may use the stored image data to review the images in non-real time such as, for example, for diagnosis or review. In other embodiments, the practitioner may retrieve a stored image and compare it with a current (or more recently stored image) to determine whether a patient condition has changed.

In further embodiments, the system can be configured such that a user can identify an area of interest or portion of the displayed image that he or she would like to enlarge. The user can make this selection by a pointing device, touchscreen display, or other user input. The system using the known mapping can determine which image sensor corresponds to the selected area on the display. The system can then select the image data from that sensor (or group of sensors) and process that image data for display. Because the image data from a single sensor (or number of sensors less than the total) is of a smaller pixel size than image data from the entire array, less compression is needed to display the selected image data on the display monitors. Accordingly, a high-resolution image, and sometimes at the native pixel level, can be provided for the area of interest.

Before describing the image processing and image capture technology in detail, it may be useful to describe an example application with which embodiments of the image processing and capture technology disclosed herein may be implemented. FIG. 2 is a diagram illustrating an example medical imaging system 200. This example medical imaging system 200 incudes one or more medical image display systems 202, a surgical camera system 204, and a medical image processing system 206.

In operation, images of biological tissue, a body cavity, or other sample are captured by surgical camera system 204. The surgical camera system 204 may include, for example, an endoscope or other device configured to capture medical images of biological tissue, an organ, a body cavity or other sample. The captured images, whether still or motion picture images, can be transferred by a wired or wireless communication link 210 to medical image processing system 206 for desired image processing. Image processing system 206 can perform image processing such as, for example, executing a clarity or image quality processing, data compression for storage or display, decompression, and so on.

The processed images can then be provided to one or more medical image display systems 202 by a communication or datalink 208. Although the medical image processing system 206 and the surgical camera system 204 may be communicatively coupled to one another using a separate communication link 210 as shown, in other embodiments, they can communicate using the same communication link or bus 208 (this alternative not illustrated).

The medical image display systems 202 may include one or more display devices configured to display images captured by the medical imaging system. These displays can include, for example, a plasma display, a Liquid Crystal Display (LCD), a Light Emitting Diode (LED) display, or any display suitable for rendering images for viewing by the health care practitioners utilizing the system. Though multiple medical image display systems 202, are shown in FIG.

2, it is noted that in some embodiments a single medical image display system 202 may be provided.

In some embodiments, the images displayed by medical image display systems 202 can include still or video images of the biological tissue, organ, body cavity or other sample captured by the endoscope. In some embodiments, these may be referred to as medical images. These images can be captured using a camera (such as, for example, camera system 204) or other image capture device.

In the example medical imaging environment, the medical image display systems 202 can support multiple perspectives, or views. For example, the first view may comprise "enhanced" video, e.g., video that has been magnified, filtered, etc.; and the second view may comprise "raw" video, e.g., video that has not been magnified, filtered, etc. By way of a more generalized example, the medical image display systems 202 can be configured to each display a selected view that may be the same as or different from the other displays, whether video or still, of the entire image or an AOI of a given size or enlargement.

As another example, the medical image display systems 202 can be 'tiled' together to provide the entire image (video or still) or AOI across multiple displays. Configuring and driving the displays as a tiled mural of displays can create a tiled display surface having a pixel array larger in size than that of a single display monitor. Creating this mural of displays allows the health care practitioners flexibility in viewing different portions of the sample. For example, the mural of displays may be configured with a sufficient number of displays to allow a contiguous representation of a full size image captured by the sensor array. Also, the mural of displays can be configured to present a contiguous representation of a full size image captured by the proper subset of sensors in the sensor array.

As these examples illustrate, in some embodiments, the medical image display systems 202 can be configured as a matrix of displays to allow high resolution images from the image sensors to be displayed on the display systems in a tiled mural fashion, or to allow different images or AOIs, or different perspectives or levels of magnification to be displayed on different displays or subsets of displays in the group.

In other embodiments, the multiple displays do not need to be arranged all together in a matrix fashion, but one or more of the monitors can be located at determined disparate points in the operating theater or even in other healthcare environments. Display systems can even be located remote from the treatment facility, whether configured individually or in groups. In various embodiments, different users or healthcare practitioners can access the system through a user interface and control one or more individual monitors of the entire set of monitors. Accordingly, a given practitioner may select a given AOI or AOIs of interest to that practitioner and control the display of those AOI(s) on his or her assigned display(s). The system can be configured to display different views, different levels of magnification or different AOIs on different monitors if desired. Additionally, the users can select whether to review still images or a live video feed on the various monitors. Accordingly, the system can be configured to provide multiple different sessions for different practitioners in the same or in different locations.

In various embodiments, the medical image display system(s) 202 can include a graphical user interface (GUI) to allow users to control these views and other aspects of the medical imaging system 200. Examples of such user interfaces are described in more detail below.

Having thus described an example implementation of the technology disclosed herein, a more detailed description of various aspects of this technology is now provided.

FIG. 3 is a diagram illustrating an example of an endoscopic image capture device in accordance with one embodiment of the technology disclosed herein. Particularly, the example illustrated in FIG. 3 depicts an example implementation of the distal end of an insertion tube of an endoscopic camera. In various embodiments, this image capture device 300 can be provided to implement surgical camera system 204. In this example, endoscopic image capture device 300 includes illumination fibers 304, lenses 306, a window 308, and an image sensor 310. This figure also includes a sample to be imaged which, in this example, is the biological tissue 312.

The illumination fibers 304 may include optical fibers that provide illumination 314 to biological tissue 312. In some embodiments, the illumination fibers 304 are coupled to a light source (not illustrated) at the proximal end of the endoscopic image capture device 300. It is noted that although one set or group of illumination fibers 304 is illustrated at the top of the depiction, one of ordinary skill in the art will appreciate that illumination fibers 304 can be configured in multiple locations about lenses 306, window 308, and image sensor 310, or even completely surrounding the periphery of these components.

Lens system 306 in this example includes 3 lenses, 306(1), 306(2), and 306(3), which operate to transmit sample images from the sample (e.g., biological tissue 312) to the image sensor 310. In this case, the images are a result of light from illumination 314 being reflected off sample 312 in the form of reflected light 316. Although this example includes a 3-lens system, other embodiments can be implemented with other lens systems configured to transmit or project the sample image to image sensor 310. In yet other embodiments, other optical structures can be used to transmit the images from the distal end to the image sensor 310. For example, embodiments can be implemented using optical fibers or a fiber bundle in place of or in addition to a lens system.

Image sensor 310 may include one or more image sensors to capture the sample image (e.g., the reflections 316) and transform the optical signal into an electrical representation of the image. Once transformed into an electrical representation, this image information can be stored and processed as appropriate depending on the use or application. For example, this information can be transferred to a processing system such as medical image processing system 206 for processing and storage.

Image sensors 310 may include, for example, Charge Coupled Device (CCD) sensors, CMOS image sensors, electron multiplication CCD or EMCCD image sensors, or other image sensors. In various embodiments, the image sensors may be configured as a focal plane array of image sensors. Accordingly, a plurality of image sensors can be combined adjacent one another to form a sensor array.

As illustrated in FIG. 3, one aspect of this endoscopic image capture device 300 is that portions of the sample (e.g. the biological tissue) are mapped to corresponding portions of the image sensor. In embodiments where image sensor 310 is implemented as an image sensor array, individual portions of the sample are mapped to corresponding image sensors in the sensor array. For example, as shown in FIG. 3, the first image sensor set 310(1) receives reflections 316 from the third portion 312(3) of the biological tissue 312. The second image sensor set 310(2) receives reflections 316 from the second portion 312(2) of the biological tissue 312.

The third image sensor set 310(3) receives light rays corresponding to reflections 316 from the first portion 312(1) of the biological tissue 312.

As a result of this mapping, individual image sensors, or groups of image sensors, in the array can be identified as imaging particular portions of the sample being imaged. As described in more detail below, this mapping can be used to select one or more portions of the sample for viewing, effectively allowing the user to zoom in on or enlarge a portion of the entire image. In various embodiments as also described below, this can be done at a resolution higher than that of typical conventional digital zoom techniques.

Additionally, various embodiments permit multiple independent viewing sessions of image data from all or less than all of the image sensors in the array. For some embodiments, the array of image sensors comprises a focal plane array of image sensors. Each image sensor in the focal plane array of image sensors 310 may have a native pixel resolution and the effective native pixel resolution of the focal plane array may be the aggregate of the native pixel resolution of the image sensors in the focal plane array. It will be understood that the arrangement of the image sensors in the array can determine the effective native pixel resolution of the array as a whole. Depending on the embodiment, the image sensors in the array may differ in type, native pixel resolution, physical dimension, aspect ratio, and other capabilities or characteristics.

In one embodiment, assume for example that the image sensors 310 may comprise an array of sensors that achieve an effective number of pixels at or greater than 61,440×34,560 pixels. In some example applications, the display upon which the images are displayed (e.g., image display system 202) has a maximum image size of (e.g., 1920×1080 pixels), which is smaller than the pixels size of the data from the focal plane array. Accordingly, the display may not be capable of displaying all the native pixels of the image data as provided by the focal plane array of image sensors. Consequently, the image may be compressed (e.g., compression rate of 32:1) before being displayed on a display. In other words, the system may need to compress the image such that the image size is less than or equal to the capabilities of the display. Accordingly, resolution of the displayed image may be less than the resolution of the image captured at the image sensors.

Alternatively, the user may select (e.g. through the GUI) a portion of the image to be enlarged and viewed on the entire display screen, for example, in a fill-screen or fit-screen mode. In some embodiments, the portion can be selected such that it can be viewed at the native pixel resolution on the display. In some embodiments, this can be accomplished by selecting image data from one or more image sensors of the focal plane array that correspond to the section of the image that the user wishes to enlarge. In other words, a sub window of the sensor array can be selected for image processing.

For some embodiments, magnification is facilitated without loss of accuracy or acuity, or with limited loss. The magnification may be achieved, for example, by retrieving raw image data (e.g., video or static images) from only those image sensors in the array that correspond to the area selected for magnification. Because a proper subset of one or more sensors is used, the total number of pixels is smaller than that of the image from the entire array and, accordingly, the compression rate may be adjusted to reduce the amount of compression (or even eliminate compression) while still allowing the image to be properly sized for the display. In other words, the compression can be adjusted (reduced or eliminated) such that more of the raw image data of the selected area of interest is available for display. This is made possible by selecting a proper subset of image sensors from the entire image sensor array. The raw image data can contain a larger number of pixels relative to the sample area and therefore show increased details in the biological tissue being observed. The raw image data can be output to a display capable of showing images at higher, or even at the highest resolutions of the selected sensor or sensors. Accordingly, a deep dive can be made into the image, allowing small areas of interest to be displayed at maximum resolution.

Although FIG. 3 shows the image sensors 310 at the distal end of the endoscope, in various embodiments, the image sensors 310 may be placed at other locations in or near the endoscope including at the proximal end of the endoscope. For example, in one embodiment, the image sensors 310 may reside near the control handle and/or within the camera head of the endoscope.

Figure 4:
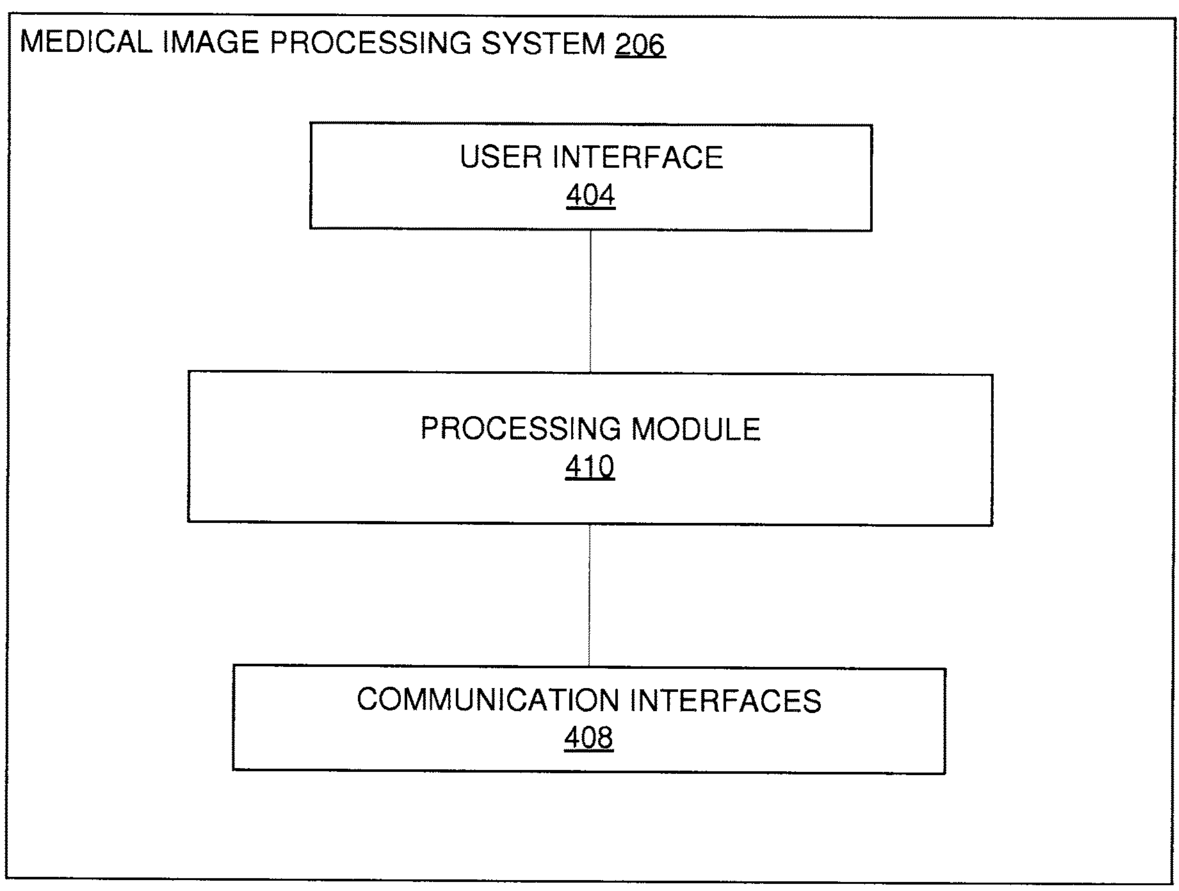
FIG. 4 is a diagram illustrating a medical image processing system in accordance with one embodiment of the technology described herein.

FIG. 4 is a diagram illustrating an example of a medical image processing system according to some embodiments. The medical image processing system 206 in this example includes one or more user interfaces 404, a processing module 410, and communications interfaces 408.

User interfaces 404 may be configured to allow a user to control various aspects of the image processing system 200, such as, for example, the medical image display system(s) 202 and/or the surgical camera system 204. User interfaces 404 can be configured to allow a user to perform operations such as, for example, (i) guide the distal end of medical imaging system 300 to a specified location such as a specific body cavity or a specific section of biological tissue; (ii) allow the user to control the camera system to capture images, select an AOI for viewing or capture, magnify an AOI, sample an AOI, sample different perspectives of the subject (different views, different magnifications, different angles, etc.), and so on; (iii) select for display one or more particular perspectives of biological tissue; and (iv) control the light source.

In various embodiments, the user interface 404 may include a keypad, keyboard, mouse or pointing device, touchscreen interface, or other user interface that allows a user to control the medical imaging system 200 or to otherwise provide input to the medical imaging system 200.

Processing module 410 can be configured to control the user interface 404 and communication interfaces 408 and to otherwise perform the processing and control for medical image processing system 206. This processing can include, for example, processing images for clarity and acuity, image compression, image enlargement or magnification, AOI selection and display, and other image processing and operational processing as further described herein. Processing module 410 can include one or more processors and associated non-transitory memory to perform these functions.

The processing module 410 may include hardware, software, and/or firmware configured to compress and/or decompress image sensor data for display. In some embodiments, processing module 410 uses compression and/or decompression algorithms to compress image sensor data from the image sensors to a size compatible with the medical image display system(s) 202. For instance, the processing module 410 may employ one or more 32:1 ratio compression algorithms to compress 61,440×31,560 pixel image sensor data into 1920×1080 pixel medical image display data.

As another example, the image sensor data compression module 412 may employ one or more 16:1 compression algorithms to compress a selected portion of the sensor data characterized by 61,440×31,560 pixels (e.g., half of the image captured by the image sensors 310) into 1920×1080 pixel medical image display data. Such 16:1 compression algorithms may effectively magnify medical image display data by a factor of two (compared to a 32:1 compression ratio) on the medical image display system(s) 202. As other examples, the image sensor data compression module 412 may employ 8:1, 4:1, 2:1, or P:Q compression ratios, where P and Q are arbitrary integers. Each of these compression ratios may compress image sensor data into medical image display data, including medical image display data having 1920×1080 pixels. Note that the 61,440×31,560 pixel image sensor size and 1920×1080 pixel medical image display size are provided as examples for illustrative purposes only. After reading this description, one of ordinary skill in the art will appreciate how systems and methods in accordance with these teachings can be implemented in systems having different numbers of image sensors in a pixel array, different image sizes and different display capabilities.

FIG. 5 is a flowchart illustrating an example process for imaging biological tissue, according to some embodiments. At step 502, the user via the user interface instructs the surgical camera system 204 to be directed to access a specific sample (e.g., a specific body cavity or specific section of tissue) and to illuminate the selected sample. At operation 504, light reflections from the selected sample are transmitted to the image sensor for image capture. Particularly, in some embodiments, light reflections from different portions of the selected sample are captured on corresponding portions of the image sensor array transformed into an image comprised of electrical signals representing the pixels of the image.

At step 506, the captured image in the form of the pixel data signals is provided to medical image processing system 206 for image processing. The processing can include applying clarifying algorithms to remove visual obfuscation from a selected portion of a medical image. More specifically, the tools used for a medical procedure may generate smoke, mist, fog, vapor, etc. that cause the biological tissue 312 to appear unclear and/or covered at least in part. The medical image view processing module 410 may employ clarifying algorithms to remove the effects of the smoke, mist, fog, vapor, etc. from medical images of the biological tissue. The medical image view processing module 410 may further use other algorithms (e.g., enhancement, variable resolution, media encoding, or fusion algorithms) to optimize viewing of medical images.

Processing may also include image compression. This compression occurs at step 508. Depending on the number of pixels of the image and the maximum pixel size and the aspect ratio of the display system on which the image is to be displayed, the captured image data may be compressed. Compression may be necessary to allow the entire image to be displayed on a display monitor having a lower resolution. In terms of the example described above, the processing system may be configured to compress the image sensor data at a resolution of 61,440×31,560 pixels to a resolution of 1920×1080 pixels for display on the medical image display system(s) 202. Once properly compressed and sized for the display device, the images can be displayed to the healthcare practitioner. This is illustrated at step 510.

As noted above, in some embodiments the systems and methods described herein can be configured to magnify or enlarge desired AOIs of the overall captured image. Magnification of images can permit a medical practitioner, such as a surgeon, to "zoom" in on portions of images provided by the surgical camera and view greater resolution in the AOI. For some embodiments, the image processing system permits an operator to locate the display area and size the AOI whether in a still image, a recorded video stream or a live video image stream.

Accordingly, in other embodiments, a proper subset of one or more of the image sensors in the image sensor array can be selected for display on the display monitors to provide an enlarged view of the AOI. The image sensor or sensors selected are those that receive the optical image (e.g., reflections) for the selected AOI. Only the image data from the selected sensors is provided to the display screen for display. Because the total image size of a proper subset of sensors is less than the total image size of the entire sensor array, the images from the selected sensors can be subjected to a lesser amount of compression. Indeed, in some embodiments, where the resolution of an image sensor matches the resolution of the display, the image for the AOI can be provided to the display with little or no compression. Accordingly, in some configurations the AOI can be viewed on the monitor with its original number of pixels, thereby achieving a higher resolution than would be achieved by a digital zoom into the same area in a compressed image. In some embodiments, depending on the native resolution of the sensors, this can be sufficient resolution to reveal details at a cellular or almost microscopic level. This deep dive capability for displaying image data at or closer to the native resolution of a sensor or proper subset of sensors presents a significant advantage over conventional digital zoom techniques.

Figure 6:
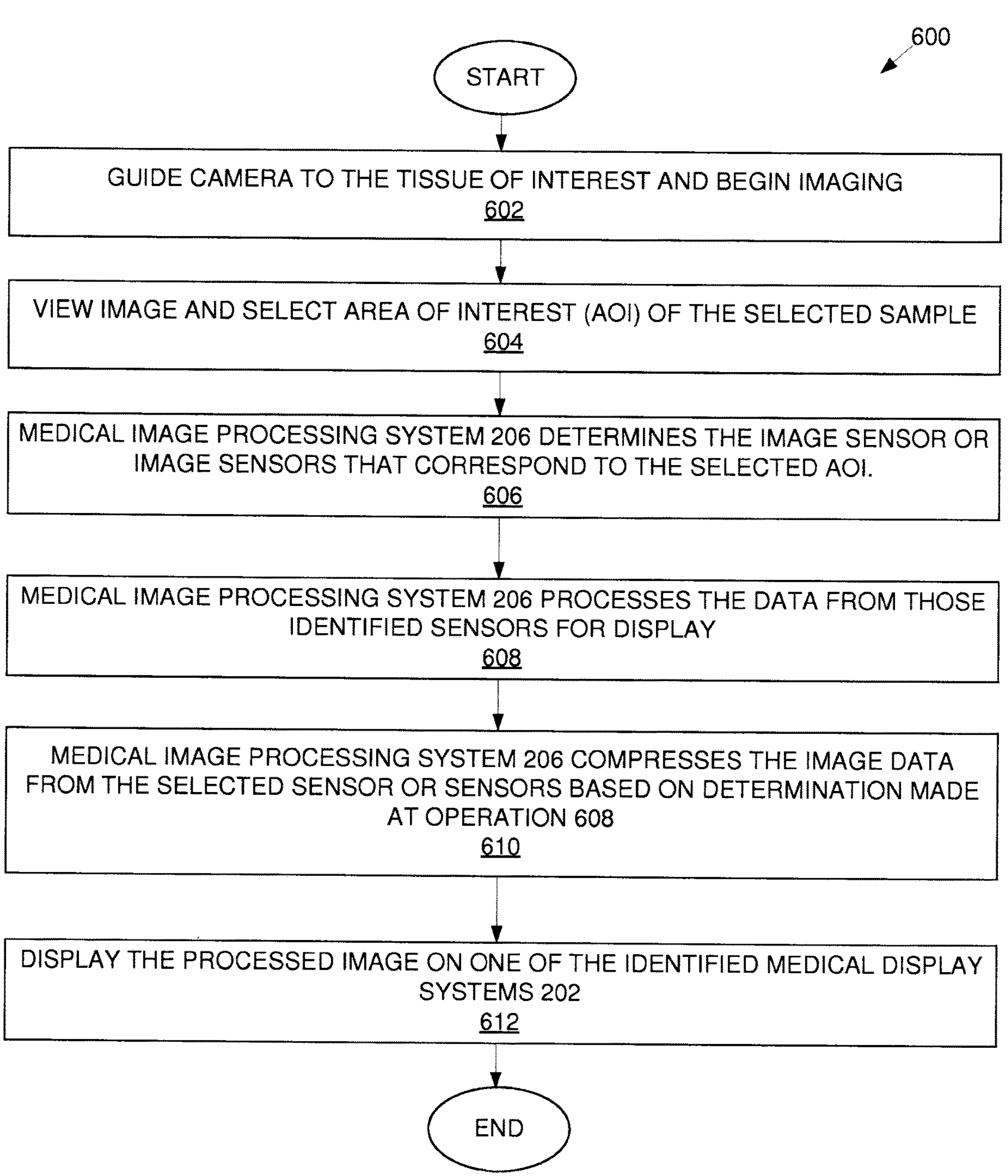
FIG. 6 is a flowchart illustrating a method for enlarging a portion of an image of biological tissue in accordance with one embodiment of the technology described herein.

FIG. 6 is a diagram illustrating an example process for enlarging or magnifying a portion of an image of biological tissue, according to some embodiments. At step 602, the endoscopic camera is guided to the tissue of interest and imaging begins. In this example, in the initial step the image captured by the full sensor array is processed, compressed as necessary, and displayed on the display screen. Alternatively, this process can be performed with stored images previously captured by the endoscopic camera. In this alternative, the stored images are retrieved and may be decompressed if necessary to process the full size image (e.g., for clarity). Like the live feed, this retrieved decompressed image can be compressed as necessary to allow the image to fit on the display.

At operation 604, a healthcare practitioner views the image and selects an AOI of the displayed image. Typically, the area of interest is a proper subset of the total area of the display screen. This can be selected, for example, using a user interface such as a pointing device, keypad, or touchscreen display. In other embodiments, AOIs may be predetermined or identified in advance for stored images, and a list of the identified AOIs maintained. For instance, a health care practitioner may review images in advance and identify particular areas of interest such as a spot or growth on tissue, parts of an organ, damaged tissue, and so on. This list can be provided to another practitioner such as, for example, a specialist or one rendering a second opinion, to allow that practitioner to select AOIs from a menu or other such list.

At operation 606, medical image processing system 206 determines the image sensor or image sensors that correspond to the selected AOI. For example, boundary and area information determined based on the input provided by the user interface allows the processing system to determine coordinates of the image that are selected as the AOI. Because the coordinates of the display screen can be mapped to corresponding coordinates on the image sensor array, the processing system can identify which image sensor, or which group of image sensors, of the array cover the selected area.

At operation 608 with the image sensor or sensors selected, medical image processing system 206 processes the data from those identified sensors for display. For example, medical image processing system 206 can determine the image size provided by the selected sensors and compare that to the maximum image size accepted by the display. In embodiments where the AOI is intended to be displayed in a sub-window (as described more fully below with reference to FIG. 7), the system can determine the maximum image size permitted by a designated sub-window in the display. In situations where the image size is greater than the capabilities of the display, image processing system 206 compresses the image so that it can fit on the display or in the sub-window. In situations where the image size is not greater than the display pixel size, image processing system 206 may provide the image for rendering in its native pixel format.

At operation 610, medical image processing system 206 compresses the image data from the selected sensor or sensors, if needed, based on the determination made at operation 608. At operation 612 the processed image is displayed on one of the identified medical display systems 202.

Consider an example where the image sensor array has 32 image sensors and the native pixel size of an individual sensor in the array is approximately 2 megapixels. Where the AOI corresponds to the area covered by one image sensor, and the image sensor has an aspect ratio equivalent to that of the display (e.g., 1920×1080 pixels) in this example, little or no compression is needed to display the AOI. On the other hand, if a conventional digital zoom methodology were applied, the 64 megapixel image from the 32 image sensors would have been compressed at a rate of 32:1 to fit on the 1920×1080 display. This roughly corresponds to approximately 1/32 of the original resolution. Accordingly, in this example, the AOI using a conventional digital zoom is approximately 1/32 the resolution of the AOI that would be selected using the process described with FIG. 6.

As described above, portions of the entire image can be selected for enlargement based on a mapping between image sensors on the sensor array and corresponding portions of the sample being imaged. As noted above, the image sensor corresponding to desired sample portion can be selected in real time as the image is transmitted from the image sensor (whether a still image or an image stream) or it can be selected from stored image data.

To facilitate identification of image data corresponding to individual sensors in the array, sensor information can be stored along with its corresponding image data when the data is stored in memory. Accordingly, when the user selects an AOI and the system identifies the sensors corresponding to that AOI, the system can use that sensor information to retrieve the data from storage. Preferably, the data is stored at the native resolution so image detail is not lost due to storage. In some applications, data may be compressed for storage. In these circumstances, the data be may decompressed when retrieved from storage prior to processing for display. Lossless forms of compression can be preferred such that the data is restored to its original resolution.

FIG. 7 is a diagram illustrating an example use of one or more example image processing algorithms such as those described above with respect to FIGS. 5 and 6. As shown in this example, the system can further be configured such that the user may select a portion of an image on a display (e.g., a sub-window). The sub-window can be used to display an AOI. Also, the selected portion can be processed through a clarifying algorithm to remove visual obfuscation (e.g., smoke, mist, fog, vapor, etc.) from that portion. Algorithms (e.g., enhancement, variable resolution, media encoding, or fusion algorithms) may be sequenced to optimize viewing. In the event that an operator (e.g., surgeon) desires more detail, they can utilize the enlarge feature to present more pixels by way of lowering compression or selecting image sensors in the array of image sensors that corresponds to the sub-window (e.g., selected area of interest). A lower compression may be utilized to present a smaller image segment in the same display area at a higher resolution image. Various embodiments may permit an operator (e.g., surgeon) to progressively "dive" all the way to the native pixel resolution of the image provided by the array of image sensors. Digital zoom may be utilized thereafter if necessary (e.g., when a resolution greater than the native pixel resolution of each image sensor is needed).

In various embodiments, multiple display screens can be provided and arranged as appropriate for the environment. For example, one or more display screens can be placed at one or more operational stations in the operating theater to allow various healthcare professionals performing various tasks to select and access particular AOIs that might be of interest to them. As another example, multiple display screens can be arranged as a matrix of displays to enable viewing of multiple AOIs, angles or perspectives by a single healthcare practitioner.

In the example illustrated in FIG. 8, a lens receives an image of a biological tissue under observation of a surgical camera, focuses the image onto a focal plane array of image sensors, which in turn can electronically relay the image to a display for viewing (as shown) or recording. Before the image from the array of image sensors is provided to a display, it may be processed (e.g., enhanced) upon on a user's request. The focal plane array of image sensors may have an effective native pixel resolution based on the native pixel resolution of the individual image sensors in the array and their particular arrangement. As shown in FIG. 8, and continuing with the example used above, a focal plane array of image sensors may achieve an effective native pixel resolution of 61440×34560 pixels and provide image data at such a resolution. Where the display upon which the images are displayed has a resolution (e.g., 1920×1080 pixels) lower than that of the image data (e.g., 61440×34560 pixels) from the focal plane array of image sensors, the display may not be capable of displaying all the native pixels of the image data as provided by the focal plane array of image sensors. Consequently, the viewer may view portions of the image (provided by the image data) at their native pixels or the image may be compressed (e.g., compress pixels from 32:1) before being displayed on a display (e.g., compressed such that resolution of the entire image is less or equal to the resolution capabilities of the display). For some embodiments, a portion of the image from the focal plane array of image sensors can be selected (e.g., selected as a sub-window) for image processing (e.g., image enhancement) of the selected portion. Processing of the selected portion may be achieved with no change in resolution to the overall image or the selected portion.

FIG. 9 is a diagram illustrating an example array of image sensors observing biological tissue in accordance with some embodiments. In comparison to FIG. 8, FIG. 9 illustrates how a selected portion (e.g., in a sub-window) may be magnified (e.g., zoomed-in) by selecting to receive image data from only those image sensors in the focal plane array of image sensors that correspond to the selected portion (e.g., that are observing the selected area of interest), thereby utilizing the native resolution of the set of image sensors to achieve the magnification. The selected portion may be magnified by adjusting the compression utilized to fit the selected portion for display.

By performing magnification in these ways, various embodiments utilize the native resolution of image sensors to achieve magnification without the need for digital magnification. For some embodiments, the selected image area of interest (AOI) is scaled to fit the selected display image area. The "zoom in" may occur, for example, by reducing the native image AOI. For some embodiments, the number of pixels in the display sub-window is used to determine how much compression, if any, is required to fit the selected AOI raw image data (e.g., from select image sensors in the array corresponding to the AOI) inside the display sub-window.

Figure 10:
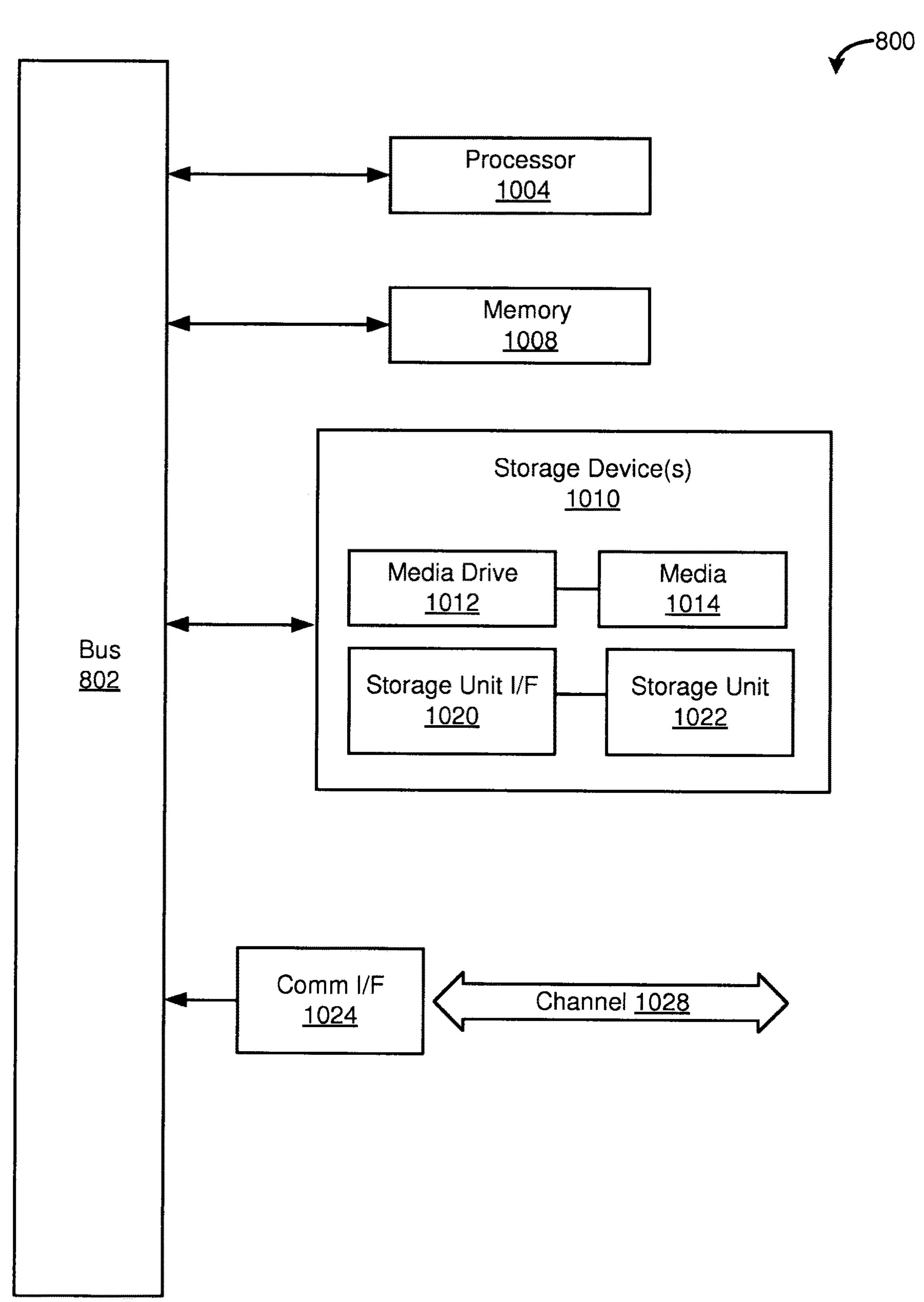
FIG. 10 illustrates an example computing module that may be used in implementing various features of embodiments of the disclosed technology.

As used herein, the term module might describe a given unit of functionality that can be performed in accordance with one or more embodiments of the technology disclosed herein. As used herein, a module might be implemented utilizing any form of hardware, software, or a combination thereof. For example, one or more processors, controllers, ASICs, PLAS, PALS, CPLDs, FPGAs, logical components, software routines or other mechanisms might be implemented to make up a module. In implementation, the various modules described herein might be implemented as discrete modules or the functions and features described can be shared in part or in total among one or more modules. In other words, as would be apparent to one of ordinary skill in the art after reading this description, the various features and functionality described herein may be implemented in any given application and can be implemented in one or more separate or shared modules in various combinations and permutations. Even though various features or elements of functionality may be individually described or claimed as separate modules, one of ordinary skill in the art will understand that these features and functionality can be shared among one or more common software and hardware elements, and such description shall not require or imply that separate hardware or software components are used to implement such features or functionality.

Where components or modules of the technology are implemented in whole or in part using software, in one embodiment, these software elements can be implemented to operate with a computing or processing module capable of carrying out the functionality described with respect thereto. One such example computing module is shown in FIG. 10. Various embodiments are described in terms of this example-computing module 800. After reading this description, it will become apparent to a person skilled in the relevant art how to implement the technology using other computing modules or architectures.

In various embodiments, the computing module 800 represents, for example, computing or processing capabilities found within desktop, laptop and notebook computers; hand-held computing devices (PDA's, smart phones, cell phones, palmtops, etc.); mainframes, supercomputers, workstations or servers; or any other type of special-purpose or general-purpose computing devices as may be desirable or appropriate for a given application or environment. Computing module 800 might also represent computing capabilities embedded within or otherwise available to a given device. For example, a computing module might be found in other electronic devices such as, for example, digital cameras, navigation systems, cellular telephones, portable computing devices, modems, routers, WAPs, terminals and other electronic devices that might include some form of processing capability.

Computing module 800 might include, for example, one or more processors, controllers, control modules, or other processing devices, such as a processor 804. Processor 804 might be implemented using a general-purpose or special-purpose processing engine such as, for example, a microprocessor, controller, or other control logic. In the illustrated example, processor 804 is connected to a bus 802, although any communication medium can be used to facilitate interaction with other components of computing module 800 or to communicate externally.

Computing module 800 might also include one or more memory modules, simply referred to herein as main memory 808. For example, preferably Random Access Memory (RAM) or other dynamic memory might be used for storing information and instructions to be executed by processor 804. Main memory 808 might also be used for storing temporary variables or other intermediate information during execution of instructions to be executed by processor 804. Computing module 800 might likewise include a read only memory ("ROM") or other static storage device coupled to bus 802 for storing static information and instructions for processor 804.

The computing module 800 might also include one or more various forms of information storage mechanism 810, which might include, for example, a media drive 812 and a storage unit interface 820. The media drive 812 might include a drive or other mechanism to support fixed or removable storage media 814. For example, a hard disk drive, a floppy disk drive, a magnetic tape drive, an optical disk drive, a CD or DVD drive (R or RW), or other removable or fixed media drive might be provided. Accordingly, storage media 814 might include, for example, a hard disk, a floppy disk, magnetic tape, cartridge, optical disk, a CD or DVD, or other fixed or removable medium that is read by, written to, or accessed by media drive 812. As these examples illustrate, the storage media 814 can include a computer usable storage medium having stored therein computer software or data.

In alternative embodiments, information storage mechanism 810 might include other similar instrumentalities for allowing computer programs or other instructions or data to be loaded into computing module 800. Such instrumentalities might include, for example, a fixed or removable storage unit 822 and an interface 820. Examples of such storage units 822 and interfaces 820 can include a program cartridge and cartridge interface, a removable memory (for example, a flash memory or other removable memory module) and memory slot, a PCMCIA slot and card, and other fixed or removable storage units 822 and interfaces 820 that allow software and data to be transferred from the storage unit 822 to computing module 800.

Computing module 800 might also include a communications interface 824. Communications interface 824 might be used to allow software and data to be transferred between computing module 800 and external devices. Examples of communications interface 824 might include a modem or softmodem, a network interface (such as an Ethernet, network interface card, WiMedia, IEEE 802.XX or other interface), a communications port (such as for example, a USB port, IR port, RS232 port Bluetooth® interface, or other port), or other communication interface. Software and data transferred via communications interface 824 might typically be carried on signals, which can be electronic, electromagnetic (which includes optical) or other signals capable of being exchanged by a given communications interface 824. These signals might be provided to communications interface 824 via a channel 828. This channel 828 might carry signals and might be implemented using a wired or wireless communication medium. Some examples of a channel might include a phone line, a cellular link, an RF link, an optical link, a network interface, a local or wide area network, and other wired or wireless communications channels.

In this document, the terms "computer program medium" and "computer usable medium" are used to generally refer to media such as, for example, memory 808, storage unit 822, media 814, and channel 828. These and other various forms of computer program media or computer usable media may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions might enable the computing module 800 to perform features or functions of the disclosed technology as discussed herein.

While various embodiments of the disclosed technology have been described above, it should be understood that they have been presented by way of example only, and not of limitation. Likewise, the various diagrams may depict an example architectural or other configuration for the disclosed technology, which is done to aid in understanding the features and functionality that can be included in the disclosed technology. The disclosed technology is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the technology disclosed herein. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

What is claimed is:

1. A medical imaging system comprising:

a surgical camera configured to capture an image of a selected subject via a plurality of image sensors, wherein each image is mapped to a corresponding portion of the selected subject;

an optical system used to transmit said images from an objective lens to said plurality of image sensors;

a user input device configured to accept input from a system user via a user interface to select an area of interest (AOI) of the selected subject wherein each of the plurality of image sensors focus on differing areas of the selected subject to provide a greater resolution of the selected subject;

an image processing module comprising one or more processors, a first input configured to receive images captured by the surgical camera via connection to an external communication medium, a second input configured to receive the user input identifying an AOI via the user interface, and an output including raw image data to a display monitor wherein said raw image data is representative of uncompressed and unprocessed video or static image data captured by the surgical camera; the image processing module configured to select a proper subset of images, via the one or more processors, that is mapped to the AOI of the selected subject by determining which image sensor or group of image sensors corresponds to the AOI based on a known mapping between portions of the displayed image and the plurality of image sensors, and to provide an image of the AOI, captured by a selected proper subset of fewer than all of the plurality of image sensors at the output;

wherein said imaging processing module comprises logic for a plurality of purposes including stitching various image data from said plurality of image sensors into a single picture, compressing high resolution images to a format suitable for display devices that have lower resolutions, and providing image enhancement;

wherein users are enabled to use stored image data in non-real time;

the display monitor having an input coupled to the output of the image processing module to display the image of the AOI; and a clarifying algorithm configured to process said first input, wherein said processing comprises removing visual obfuscation;

wherein said image processing module further comprises an image sensor data compression module configured to employ one or more compression algorithms which, when employed, compress image data from the selected proper subset of image sensors corresponding to the AOI with a reduced amount of compression relative to image data outside the AOI.

2. The medical imaging system of claim 1, wherein the image processing module is further configured to determine a pixel size of the display monitor and to apply data compression at a first compression rate to reduce an image size of the captured image of the selected subject to a size that is no greater than the resolution of the display monitor.

3. The medical imaging system of claim 2, wherein the image processing module is further configured to determine the image size of the image of the AOI, and to apply data compression at a second compression rate to reduce an image size of the image of the AOI to a size that is no greater than the pixel size of the display monitor, wherein the second compression rate is less than the first compression rate.

4. The medical imaging system of claim 1, wherein the image processing module is further configured to determine an image size of the image of the AOI, and to send the image of the AOI at its native image resolution if the image size of the image of the AOI is no greater than the pixel size of the display monitor.

5. The medical imaging system of claim 1, wherein the proper subset of images comprises a quantity of one or more of the images that is less than the total quantity of images captured.

6. The medical imaging system of claim 1, wherein the surgical camera further comprises illumination structures.

7. The medical imaging system of claim 6, wherein the illumination structures comprise illumination fibers.

8. The medical imaging system of claim 1, wherein the image processing module is further configured to determine a pixel size of a sub-window of the display monitor and to apply data compression at a first compression rate to reduce an image size of the captured image of the selected subject to a size that is no greater than the resolution of the display monitor.

9. The medical imaging system of claim 8, wherein the image processing module is further configured to determine the image size of the image of the AOI, and to apply data compression at a second compression rate to reduce an image size of the image of the AOI to a size that is no greater than the pixel size of the sub-window of the display monitor, wherein the second compression rate is less than the first compression rate.

10. The medical imaging system of claim 1, wherein the image processing module is further configured to determine an image size of the image of the AOI, and to send the image of the AOI at its native image resolution if the image size of the image of the AOI is no greater than the pixel size of a sub-window of the display monitor.

11. The medical imaging system of claim 1, wherein the display monitor comprises a plurality of display monitors coupled to the output of the image processing module.

12. The medical imaging system of claim 11, wherein the plurality of display monitors is configured to display different views of the selected subject on different monitors of the plurality of display monitors.

13. The medical imaging system of claim 12, wherein the different views comprise different AOIs of the selected subject.

14. The medical imaging system of claim 11, wherein the plurality of display monitors is configured as a mural of displays to allow a tiled display surface having a pixel size larger in size than that of a single display monitor, and wherein each display monitor is arranged to formulate the mural.

15. The medical imaging system of claim 14, wherein the mural of displays is configured with a sufficient number of displays to allow a contiguous representation of a full-size image captured of the selected subject.

16. The medical imaging system of claim 14, wherein the mural of displays is configured to present a contiguous representation of a full size image captured by the proper subset of captured images.

17. The medical imaging system of claim 11, wherein the plurality of display monitors are configured to display different views, different levels of magnification or different AOIs on different display monitors of the plurality of display monitors.

18. The medical imaging system of claim 17, the display monitors are configured to provide different sessions for different practitioners in the same or in different locations.

19. The medical imaging system of claim 1, wherein the surgical camera comprises CMOS image sensors, CCDs, or EMCCDs.

20. A medical imaging system comprising:

a surgical camera for capturing an image of a selected subject via a plurality of image sensors, wherein each image is mapped to a corresponding portion of the selected subject;

an optical system used to transmit said images from an objective lens to said plurality of image sensors;

a user input device comprising at least one of: (i) a user-operated pointing device or (ii) a touchscreen device, the user input device being configured to allow a user to control said medical imaging system or provide input to said system and being further configured to receive a user input identifying an area of interest (AOI) of the selected subject;

wherein each of the plurality of image sensors focus on differing areas of the selected subject to provide a greater resolution of the selected subject;, and wherein each of the plurality of image sensors captures raw image data, wherein said raw image data is representative of uncompressed and unprocessed video or static image data;

wherein, in response to the identified AOL, a proper subset of images that are mapped to the AOI of the selected subject are selected by determining which image sensor or group of image sensors corresponds to the AOI based on a known mapping between portions of the displayed image and the plurality of image sensors, to provide an image of the AOI captured by the selected proper subset of image sensors for display;

wherein receiving images captured by the image sensor, or said image data, can be processed by an image processing module, wherein said imaging processing module comprises logic for a plurality of purposes including stitching various image data from said plurality of image sensors into a single picture, compressing high resolution images to a format suitable for display devices that have lower resolutions, and providing image enhancement;

wherein image data from the selected proper subset of image sensors corresponding to the AOI is compressed with a reduced amount of compression relative to image data outside the AOI; and wherein users are enabled to use stored image data in non-real time.

* * * * *